(12) United States Patent
Lewis et al.

(10) Patent No.: US 8,158,104 B2
(45) Date of Patent: Apr. 17, 2012

(54) UZM-7 ALUMINOSILICATE ZEOLITE, METHOD OF PREPARATION AND PROCESSES USING UZM-7

(75) Inventors: Gregory J. Lewis, Santa Cruz, CA (US); Mark A. Miller, Niles, IL (US); Lisa M. Knight, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/172,453

(22) Filed: Jun. 29, 2011

(65) Prior Publication Data

US 2012/0004484 A1 Jan. 5, 2012

Related U.S. Application Data

(60) Provisional application No. 61/360,586, filed on Jul. 1, 2010.

(51) Int. Cl.
*C01B 39/48* (2006.01)
*C01B 39/04* (2006.01)

(52) U.S. Cl. .......... 423/705; 423/707; 423/718

(58) Field of Classification Search .......... 423/705, 423/707, 718
See application file for complete search history.

(56) References Cited

U.S. PATENT DOCUMENTS

| | | | |
|---|---|---|---|
| 4,310,440 A | 1/1982 | Wilson et al. | |
| 4,440,871 A | 4/1984 | Lok et al. | |
| 4,870,222 A | 9/1989 | Bakas et al. | |
| 5,157,196 A | 10/1992 | Crossland et al. | |
| 5,157,197 A | 10/1992 | Cooper et al. | |
| 6,388,159 B1 * | 5/2002 | Jan et al. | 585/481 |
| 6,613,302 B1 * | 9/2003 | Moscoso et al. | 423/718 |
| 6,756,030 B1 * | 6/2004 | Rohde et al. | 423/718 |
| 6,776,975 B2 | 8/2004 | Wilson et al. | |
| 7,578,993 B2 | 8/2009 | Lewis et al. | |
| 7,713,513 B2 * | 5/2010 | Jan et al. | 423/718 |
| 7,744,850 B2 | 6/2010 | Miller et al. | |

OTHER PUBLICATIONS

Lewis, Experimental Charge Density Matching approach to Zeolite Synthesis, 2004, Studies in Surface Science and Catalysis, pp. 364-372, vol. 154 A.

* cited by examiner

*Primary Examiner* — David M Brunsman
(74) *Attorney, Agent, or Firm* — David J Piasecki

(57) ABSTRACT

A new family of crystalline aluminosilicate zeolites has been synthesized designated UZM-7. These zeolites are represented by the empirical formula.

$$M_m^{n+}R_r^{p+}Al_{(1-x)}E_xSi_yO_z$$

where M is an alkali, alkaline earth, or rare earth metal such as lithium, potassium and barium, R is an organoammonium cation such as the choline or the diethyldimethylammonium cation and E is a framework element such as gallium. These zeolites are characterized by unique x-ray diffraction patterns and compositions and have catalytic properties for carrying out various hydrocarbon conversion processes.

21 Claims, No Drawings

UZM-7 ALUMINOSILICATE ZEOLITE, METHOD OF PREPARATION AND PROCESSES USING UZM-7

STATEMENT OF PRIORITY

This application claims priority to U.S. Application No. 61/360,586 which was filed on Jul. 1, 2010, the contents of which are hereby incorporated by reference in its entirety.

FIELD OF THE INVENTION

This invention relates to a new family of aluminosilicate zeolites designated UZM-7. They are represented by the empirical formula of:

$$M_m^{n+}R_r^{p+}Al_{1-x}E_xSi_yO_z$$

where M is an exchangeable cation such as barium or lithium, R is an organoammonium cation such as choline or diethyldimethylammonium and E is a framework element such as gallium.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

One particular zeolite, designated UZM-22, was first disclosed by Miller in 2010, see U.S. Pat. No. 7,744,850. This patent describes the synthesis of UZM-22 from a choline structure directing agent in combination with either Li, Sr, or both cations, using the Charge Density Mismatch (CDM) approach to zeolite synthesis as described in U.S. Pat. No. 7,578,993. The UZM-22 zeolite has the MEI structure as defined by Database of Zeolite Structures, http://www.iza-structure.org/databases, which consists of 1-dimensional 12-ring pores with a 7 Å aperture, along with a perpendicular 7-ring pore system. This promising result inspired further work with the choline structure directing agent along with various combinations of alkali and alkaline earth cations, using the CDM approach along with combinatorial high throughput synthesis methods. The screen of the choline-alkali-alkaline earth aluminosilicates yielded many known zeolite structures, including OFF, ERI, LTL, FAU, FER, LTA, CHA, BPH, MEI, and others. Several new zeolite structures were also observed, including UZM-7, which is the subject of present invention.

The applicants have successfully prepared a new family of materials designated UZM-7. The topology of UZM-7 is unique as determined by x-ray diffraction. The diffraction peaks for the UZM-7 materials are typically very broad, indicative of a small crystallite material. The materials are prepared via the use of a simple commercially available structure directing agents, such as choline hydroxide, $[HO(CH_2)_2NMe_3]^+OH^-$, in concert with small amounts of $Ba^{2+}$ and $Li^+$ together, using the CDM approach to zeolite synthesis.

SUMMARY OF THE INVENTION

As stated, the present invention relates to a new aluminosilicate zeolite designated UZM-7. Accordingly, one embodiment of the invention is a microporous crystalline zeolite having a three-dimensional framework of at least $AlO_2$ and $SiO_2$ tetrahedral units and an empirical composition in the as synthesized and anhydrous basis expressed by an empirical formula of:

$$M_m^{n+}R_r^{p+}Al_{1-x}E_xSi_yO_z$$

where M is at least one exchangeable cation selected from the group consisting of alkali, alkaline earth, and rare earth metals, "m" is the mole ratio of M to (Al+E) and varies from 0 to about 2.0, R is an organoammonium cation selected from the group consisting of choline, ethyltrimethylammonium ($ETMA^+$), diethyldimethylammonium ($DEDMA^+$), trimethylpropylammonium, trimethylbutylammonium, dimethyldiethanolammonium, tetraethylammonium ($TEA^+$), tetrapropylammonium ($TPA^+$), hexamethonium, and mixtures thereof, "r" is the mole ratio of R to (Al+E) and has a value of about 0.25 to about 4.0, "n" is the weighted average valence of M and has a value of about 1 to about 3, "p" is the weighted average valence of R and has a value of about 1 to 2, E is an element selected from the group consisting of gallium, iron, boron and mixtures thereof, "x" is the mole fraction of E and has a value from 0 to about 1.0, "y" is the mole ratio of Si to (Al+E) and varies from greater than 1.0 to about 10 and "z" is the mole ratio of O to (Al+E) and has a value determined by the equation:

$$z=(m \cdot n+r \cdot p+3+4 \cdot y)/2$$

and is characterized in that it has the x-ray diffraction pattern having at least the d-spacings and intensities set forth in Table A:

TABLE A

| 2Θ | d(Å) | I/I0% |
|---|---|---|
| 6.79-8.03 | 13.00-11.00 | m-vs |
| 11.56-12.11 | 7.65-7.30 | w-s |
| 19.07-20.4 | 4.65-4.35 | m-s |
| 23.02-24.23 | 3.86-3.67 | m-vs |
| 26.43-28.13 | 3.37-3.17 | w-m |
| 30.48-31.94 | 2.93-2.80 | m-vs | and is thermally stable up to a temperature of greater than 500° C.

Another embodiment of the invention is a process for preparing the crystalline microporous zeolite described above. The process comprises forming a reaction mixture containing reactive sources of M, R, Al, Si and optionally E and heating the reaction mixture at a temperature of about 60° C. to about 175° C. for a time sufficient to form the zeolite, the reaction mixture having a composition expressed in terms of mole ratios of the oxides of:

$$aM_{2/n}O:bR_{2/p}O:1-cAl_2O_3:cE_2O_3:dSiO_2:eH_2O$$

where "a" has a value of about 0.0 to about 4, "b" has a value of about 1.0 to about 30, "c" has a value of 0 to about 1.0, "d" has a value of about 2 to about 30, "e" has a value of about 20 to about 2000.

Yet another embodiment of the invention is a hydrocarbon conversion process using the above-described zeolite. The process comprises contacting the hydrocarbon with the zeolite at conversion conditions to give a converted hydrocarbon.

DETAILED DESCRIPTION OF THE INVENTION

Applicants have prepared an aluminosilicate zeolite with a new topological structure, which has been designated UZM-7. The instant microporous crystalline zeolite (UZM-7) has an empirical composition in the as-synthesized form and on an anhydrous basis expressed by the empirical formula:

$$M_m^{n+}R_r^{p+}Al_{1-x}E_xSi_yO_z$$

where M is at least one exchangeable cation and is selected from the group consisting of alkali, alkaline earth, and rare earth metals. Specific examples of the M cations include but are not limited to lithium, sodium, potassium, rubidium, cesium, calcium, strontium, barium, lanthanum, ytterbium and mixtures thereof. R is an organoammonium cation, examples of which include but are not limited to the choline cation, $[(CH_3)_3N(CH_2)_2OH]^+$, ETMA$^+$, DEDMA$^+$ trimethylpropylammonium, trimethylbutylammonium, dimethyldiethanolammonium, TEA$^+$, TPA$^+$, hexamethonium and mixtures thereof and "r" is the mole ratio of R to (Al+E) and varies from about 0.25 to about 4.0, while "p" is the weighted average valence of R and varies from 1 to about 2. The value of "n" which is the weighted average valence of M varies from about 1 to about 3 while "m" is the mole ratio of M to (Al+E) and varies from 0.0 to about 2. The ratio of silicon to (Al+E) is represented by "y" which varies from about 1 to about 10. E is an element which is tetrahedrally coordinated, is present in the framework and is selected from the group consisting of gallium, iron and boron. The mole fraction of E is represented by "x" and has a value from 0 to about 1.0, while "z" is the mole ratio of O to (Al+E) and is given by the equation:

$$z = (m \cdot n + r \cdot p + 3 + 4 \cdot y)/2$$

Where M is only one metal, then the weighted average valence is the valence of that one metal, i.e. +1 or +2. However, when more than one M metal is present, M is given by:

$$M_m^{n+} = M_{m1}^{(n1)+} + M_{m2}^{(n2)+} + M_{m3}^{(n3)+} + \ldots$$

$$M_m^{n+} = M_{m1}^{(n1)+} + M_{m2}^{(n2)+} + M_{m3}^{(n3)+} + \ldots$$

and the weighted average valence "n" is given by the equation:

$$n = \frac{m1 \cdot n1 + m2 \cdot n2 + m3 \cdot n3 + \ldots}{m1 + m2 + m3 + \ldots}$$

Similarly, where R is only one organoammonium cation, then the weighted average valence is the valence of that one organoammonium ion, i.e. +1 or +2. However, when more that one R organoammonium cation is present, $R_r^{p+}$ is given by:

$$R_r^{p+} = R_{r1}^{(p1)+} + R_{r2}^{(p2)+} + R_{r3}^{(p3)+} + \ldots$$

and the weighted average valence "p" is given by the equation:

$$p = \frac{r1 \cdot p1 + r2 \cdot p2 + r3 \cdot p3 + \ldots}{r1 + r2 + r3 + \ldots}$$

The microporous crystalline zeolite, UZM-7, is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals include the halide salts, nitrate salts, acetate salts, and hydroxides of the respective alkali or alkaline earth metals. R is an organoammonium cation selected from the group consisting of choline, ETMA, DEDMA, TEA, TPA, trimethylpropylammonium, trimethylbutylammonium, dimethyldiethanolammonium, hexamethonium and mixtures thereof, and the sources include the hydroxide, chloride, bromide, iodide and fluoride compounds. Specific examples include without limitation choline hydroxide and choline chloride, ethyltrimethylammonium hydroxide, diethyldimethylammonium hydroxide, tetraethylammonium hydroxide, tetrapropylammonium hydroxide, tetrapropylammonium chloride.

The reaction mixture containing reactive sources of the desired components can be described in terms of molar ratios of the oxides by the formula:

$$aM_{2/n}O:bR_{2/p}O:1-cAl_2O_3:cE_2O_3:dSiO_2:eH_2O$$

where "a" varies from about 0.0 to about 4.0, "b" varies from about 1.0 to about 30, "c" varies from 0 to 1.0, "d" varies from about 2 to about 30, and "e" varies from about 20 to about 2000. If alkoxides are used, it is preferred to include a distillation or evaporative step to remove the alcohol hydrolysis products. The reaction mixture is now reacted at a temperature of about 60° C. to about 175° C. and preferably from about 90° C. to about 150° C. for a period of about 1 day to about 3 weeks and preferably for a time of about 3 days to about 12 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. It should be pointed out that UZM-7 seeds can optionally be added to the reaction mixture in order to accelerate the formation of the zeolite.

A preferred synthetic approach to make UZM-7 utilizes the charge density mismatch concept, which is disclosed in U.S. Pat. No. 7,578,993 and Studies in Surface Science and Catalysis, (2004), Vol. 154A, 364-372. The method disclosed in U.S. Pat. No. 7,578,993 employs quaternary ammonium hydroxides to solubilize aluminosilicate species, while crystallization inducing agents such as alkali and alkaline earth metals and more highly charged organoammonium cations are often introduced in a separate step. The use of commercially available choline or diethyldimethylammonium hydroxides to prepare UZM-7 makes its synthesis economically attractive.

The UZM-7 aluminosilicate zeolite, which is obtained from the above-described process, is characterized by the x-ray diffraction pattern, having at least the d-spacings and relative intensities set forth in Table A below.

TABLE A

| 2Θ | d(Å) | I/I0% |
|---|---|---|
| 6.79-8.03 | 13.00-11.00 | m-vs |
| 11.56-12.11 | 7.65-7.30 | w-s |
| 19.07-20.4 | 4.65-4.35 | m-s |
| 23.02-24.23 | 3.86-3.67 | m-vs |
| 26.43-28.13 | 3.37-3.17 | w-m |
| 30.48-31.94 | 2.93-2.80 | m-vs |

As will be shown in detail in the examples, the UZM-7 material is thermally stable up to a temperature of at least 500° C.

As synthesized, the UZM-7 material will contain some of the exchangeable or charge balancing cations in its pores. These exchangeable cations can be exchanged for other cations, or in the case of organic cations, they can be removed by heating under controlled conditions. The UZM-7 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4 in U.S. Pat. No. 6,776,975 B1 which is incorporated by reference in its entirety. Properties that are modified include porosity, adsorption, Si/Al ratio, acidity, thermal stability, etc.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The crystalline UZM-7 zeolite of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The UZM-7 zeolite of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. No. 4,310,440 and U.S. Pat. No. 4,440,871 which are incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of 400° to 1200° F. (204-649° C.), preferably between 600° and 950° F. (316-510° C.). Reaction pressures are in the range of atmospheric to about 3,500 psig (24,132 kPa g), preferably between 200 and 3000 psig (1379-20,685 kPa g). Contact times usually correspond to liquid hourly space velocities (LHSV) in the range of about 0.1 hr$^{-1}$ to 15 hr$^{-1}$, preferably between about 0.2 and 3 hr$^{-1}$. Hydrogen circulation rates are in the range of 1,000 to 50,000 standard cubic feet (scf) per barrel of charge (178-8,888 std. m$^3$/m$^3$), preferably between 2,000 and 30,000 scf per barrel of charge (355-5,333 std. m$^3$/m$^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the UZM-7 composition using feedstocks such as gas oils, heavy naphthas, deasphalted crude oil residua, etc. with gasoline being the principal desired product. Temperature conditions of 850° to 1100° F., LHSV values of 0.5 to 10 and pressure conditions of from about 0 to 50 psig are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 5:1 and 30:1, a LHSV of about 0.3 to about 6 hr$^{-1}$, a temperature of about 100° to about 250° C. and pressures of about 200 to about 1000 psig. Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,894 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference.

The following examples are presented in illustration of this invention and are not intended as undue limitations on the generally broad scope of the invention as set out in the appended claims.

The structure of the UZM-7 zeolite of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 70° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks. For high throughput samples, diffraction patterns were collected on the Bruker-AXS GADDS diffractometer equipped with an area detector, which covered 2Θ=3-38°.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of $100 \times I/I_o$, the above designations are defined as:

$w=0-15; m=15-60; s=60-80$ and $vs=80-100$

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Examples 1-12

Two aluminosilicate solutions were prepared targeting the following reaction compositions:

$2.5\text{Choline OH}:2\text{SiO}_2:1\text{Al(OH)}_3:40\text{H}_2\text{O}$  Solution 1

$8\text{Choline OH}:20\text{SiO}_2:1\text{Al(OH)}_3:350\text{H}_2\text{O}$  Solution 2

The solutions were prepared by combining dissolving $Al(OH)_3$ (80 wt. %, Pfaltz and Bauer) in choline hydroxide (50 wt. %, Sigma-Aldrich) using a high speed mixer. Then the appropriate amount of water was added, followed by the addition of Ludox AS-40 (40 wt. % $SiO_2$). The reaction mixtures were homogenized via high speed stirrer and charged to and sealed in Teflon bottles. The reaction mixtures were digested at 95° C. until clear solutions were obtained. The resulting solutions were analyzed to give the following formulations (Ch=choline):

$Ch_{2.502}Si_{2.085}AlO_{6.92}*40.03H_2O$  Solution 1

$Ch_{8.15}Si_{20.26}AlO_{46.10}*346.79H_2O$  Solution 2

These solutions were used in the combinatorial experiment for the Si and Al sources for Examples 1-12; intermediate Si/Al ratios (5 and 8) were obtained by mixing appropriate amounts of these solutions. The reaction mixtures in these examples were further adjusted by the addition of choline hydroxide (50 wt. %), $LiCl*9.0H_2O$, $LiCl*30H_2O$, $NaCl*10.01H_2O$ and $Ba(OAc)_2*40H_2O$. To form the reaction mixtures, these solutions were dispensed by an automated pipettor to a 48-well Teflon block, which was agitated during reagent addition. Once the reagents were pipetted, the Teflon blocks were sealed and agitated for a half hour in a paint shaker. After this homogenization step, the Teflon blocks were sealed in a metal casing and placed in the ovens at either 100 or 150° C. at autogenous pressure. The addition order and volumes of each reagent utilized are given in Table 1 while digestion times, temperatures and reaction compositions are given in Table 2.

TABLE 1

| Addition Order/Reagents | Volumes (μL) | | | | | | | | | | | |
|---|---|---|---|---|---|---|---|---|---|---|---|---|
| | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
| 1. $Ch_{2.502}Si_{2.085}AlO_{6.92}*40.03\ H_2O$ | 378 | 913 | 916 | 171 | 814 | 916 | 913 | 331 | 378 | 814 | 916 | 817 |
| 2. $Ch_{8.15}Si_{20.26}AlO_{46.10}*346.79\ H_2O$ | 531 | | | 606 | | | | 465 | 531 | | | |
| 3. Choline hydroxide (50 wt. %) | 62 | 35 | 35 | 204 | 150 | 35 | 35 | 192 | 62 | 150 | 35 | 151 |
| 4. $NaCl*10.01\ H_2O$ | | 45 | | | 40 | | 45 | | | 40 | | |
| 5. $Ba(OAc)_2*40H_2O$ | 88 | 107 | 108 | 50 | 96 | 108 | 107 | 77 | 88 | 96 | 108 | 96 |
| 6. $LiCl*9H2O$ | 40 | | 41 | | | 41 | | 35 | 40 | | 41 | 37 |
| 7. $LiCl*30H_2O$ | | | | 69 | | | | | | | | |

TABLE 2

| | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|
| Digestion Temperature (° C.) | 100 | 100 | 100 | 100 | 100 | 100 | 100 | 100 | 100 | 100 | 150 | 150 |
| Digestion Time (days) | 11 | 11 | 11 | 11 | 11 | 6 | 6 | 6 | 6 | 6 | 3 | 3 |
| ChOH/Si | 0.8 | 1.28 | 1.28 | 0.98 | 1.58 | 1.28 | 0.8 | 1.10 | 0.8 | 1.58 | 1.28 | 1.58 |
| $H_2O$/Si | 21.6 | 23.8 | 23.9 | 23.9 | 26.1 | 23.9 | 23.9 | 23.9 | 21.6 | 26.1 | 23.9 | 26.0 |
| Si/Al | 5 | 2.09 | 2.09 | 8 | 2.09 | 2.09 | 2.09 | 5 | 5 | 2.09 | 2.09 | 2.09 |
| Na/Al | | 0.25 | | | 0.25 | | 0.25 | | | 0.25 | | |
| Ba/Al | 0.25 | 0.15 | 0.15 | 0.25 | 0.15 | 0.15 | 0.15 | 0.25 | 0.25 | 0.15 | 0.15 | 0.15 |
| Li/Al | 0.5 | | 0.25 | 0.5 | | 0.25 | | 0.5 | 0.5 | | 0.25 | 0.25 |

The products of these reactions were washed by centrifugation, freeze-dried and analyzed via powder X-ray diffraction. Each of the reactions yielded UZM-7 as the product. The diffraction lines for each product for Examples 1-12 are given in Table 3.

TABLE 3

| 2Θ | d(Å) | I/I₀% | 2Θ | d(Å) | I/I₀% | 2Θ | d(Å) | I/I₀% |
|---|---|---|---|---|---|---|---|---|
| Example 1 | | | Example 2 | | | Example 3 | | |
| 7.85 | 11.26 | s | 7.55 | 11.70 | vs | 7.50 | 11.78 | vs |
| 11.90 | 7.43 | m | 11.80 | 7.49 | m | 11.76 | 7.52 | s |
| 19.36 | 4.58 | m | 19.40 | 4.57 | m | 19.35 | 4.58 | m |
| 23.95 | 3.71 | vs | 23.40 | 3.80 | vs | 23.45 | 3.79 | s |
| 27.69 | 3.22 | w | 24.80 | 3.59 | m | 24.8 | 3.59 | m |
| 31.50 | 2.84 | m | 27.02 | 3.30 | m | 27.33 | 3.26 | m |
| 34.10 | 2.63 | m | 28.15 | 3.17 | m | 28.25 | 3.16 | m |
| | | | 31.15 | 2.87 | vs | 31.15 | 2.87 | vs |
| | | | 33.05 | 2.71 | w | 35.46 | 2.53 | w |
| | | | 35.65 | 2.52 | m | 36.09 | 2.49 | m |
| Example 4 | | | Example 5 | | | Example 6 | | |
| 7.50 | 11.78 | vs | 7.65 | 11.55 | vs | 7.50 | 11.78 | vs |
| 11.81 | 7.49 | m | 11.75 | 7.52 | m | 11.76 | 7.52 | s |
| 19.65 | 4.51 | s | 19.40 | 4.57 | m | 19.60 | 4.53 | m |
| 23.55 | 3.77 | m | 23.45 | 3.79 | vs | 23.50 | 3.78 | vs |
| 25.00 | 3.56 | m | 24.64 | 3.61 | m | 24.70 | 3.60 | s |
| 27.46 | 3.25 | m | 27.21 | 3.27 | m | 27.20 | 3.28 | m |
| 28.55 | 3.12 | m | 28.15 | 3.17 | m | 28.29 | 3.15 | m |
| 31.35 | 2.85 | vs | 31.10 | 2.87 | vs | 31.24 | 2.86 | vs |
| 35.85 | 2.50 | m | 35.71 | 2.51 | m | 35.80 | 2.51 | m |
| Example 7 | | | Example 8 | | | Example 9 | | |
| 7.65 | 11.55 | vs | 7.65 | 11.55 | vs | 7.80 | 11.33 | vs |
| 11.76 | 7.52 | s | 11.89 | 7.44 | m | 11.94 | 7.41 | m |
| 19.40 | 4.57 | m | 19.60 | 4.53 | m | 19.60 | 4.53 | m |
| 23.40 | 3.80 | m | 23.90 | 3.72 | s | 23.90 | 3.72 | vs |
| 24.80 | 3.59 | m | 27.77 | 3.21 | m | 26.80 | 3.32 | m |
| 27.23 | 3.27 | m | 31.30 | 2.86 | m | 28.30 | 3.15 | m |
| 28.15 | 3.17 | m | | | | 31.31 | 2.86 | s |
| 31.15 | 2.87 | vs | | | | 34.11 | 2.63 | m |
| 35.75 | 2.51 | m | | | | 35.89 | 2.50 | m |
| Example 10 | | | Example 11 | | | Example 12 | | |
| 7.55 | 11.7 | vs | 7.35 | 12.02 | s | 7.55 | 11.69 | vs |
| 11.84 | 7.47 | s | 11.80 | 7.49 | m | 11.85 | 7.46 | m |
| 19.45 | 4.56 | m | 19.65 | 4.51 | m | 19.65 | 4.52 | m |
| 23.40 | 3.8 | vs | 23.35 | 3.81 | vs | 23.60 | 3.77 | vs |
| 24.80 | 3.59 | m | 24.85 | 3.58 | m | 24.80 | 3.59 | m |
| 28.35 | 3.15 | m | 27.26 | 3.27 | m | 27.24 | 3.27 | m |
| 31.15 | 2.87 | vs | 28.30 | 3.15 | m | 28.35 | 3.15 | m |
| 35.70 | 2.51 | m | 31.25 | 2.86 | vs | 31.30 | 2.86 | vs |
| | | | 35.90 | 2.5 | m | 35.74 | 2.51 | m |

Example 13

An investigation with the diethyldimethylammonium (DEDMA) structure directing agent also yielded UZM-7. An aluminosilicate solution was prepared with the formulation 4.8 SiO₂:Al(OH)₃:5 DEDMAOH:84.29 H₂O. A 72.55 g aliquot of this solution was placed in a beaker. While stirring, 0.94 g of LiCl*4.10H₂O solution was added. This was followed by the addition of 1.93 g of KCl*13.28H₂O solution while stirring continued. Once the addition was completed, homogenization continued for 20 minutes. Then 15.41 g H₂O was removed from the reaction mixture by rotary evaporation. The reaction mixture was then transferred to a Teflon-lined autoclave and digested quiescently at 125° C. The reaction mixture was allowed to react for 13 days, but was also sampled after 6 days. After washing and isolating the samples they were dried and analyzed by powder x-ray diffraction. Both products were shown to be UZM-7; the diffraction lines are shown in Table 4.

TABLE 4

| Example 13, 6 d | | | Example 13, 13 d | | |
|---|---|---|---|---|---|
| 2Θ | d(Å) | I/I₀% | 2Θ | d(Å) | I/I₀% |
| 6.94 | 12.73 | s | 7.12 | 12.41 | w |
| 11.72 | 7.54 | w | 11.7 | 7.56 | w |
| 20.06 | 4.42 | s | 19.82 | 4.48 | s |
| 23.67 | 3.76 | m | 23.56 | 3.77 | vs |
| 24.66 | 3.61 | vs | 24.78 | 3.59 | vs |
| 28.26 | 3.16 | m | 28.58 | 3.12 | m |
| 31.28 | 2.86 | s | 31.28 | 2.86 | s |
| 35.79 | 2.51 | w | 36.09 | 2.49 | m |

Examples 14 and 15

For examples 14 and 15, a choline aluminosilicate solution was employed. The solution had the formulation 2.67 choline hydroxide:2 TEOS:1 Al(OsecBu)₃: 30.53 H₂O. The reaction mixture was rotovapped to remove the ethanol from the hydrolysis of TEOS. The choline aluminosilicate solution contained 1.59% Al and 3.30% Si.

Example 14

Choline aluminosilicate solution, 150 g, was placed in a beaker under a high speed stirrer. A solution was prepared by dissolving 0.93 g LiCl and 3.38 g Ba(OAc)₂ together in 20.24 g de-ionized water. This solution was added dropwise with vigorous stirring to the aluminosilicate solution. The solution eventually became cloudy and a fine suspension developed by the end of the addition. After stirring further for 2 hours, the reaction mixture was distributed among nine Teflon-lined autoclaves and digested quiescently at 95, 125, and 150° C. for various times. All of the 95 and 125° C. products were UZM-7 by x-ray diffraction. The 150° C. samples were also UZM-7, but contained some SOD impurity. The diffraction lines for the UZM-7 formed at 125° C. and a digestion time of 17 days are given in Table 5 below. Elemental analysis on this sample yielded the compositional ratios Si/Al=1.93, Ba/Al=0.15, Li/Al=0.22, and N/Al=0.47, exhibiting excellent cation balance. A sample digested at 125° C. for 10 days was calcined at 525° C. in air for 5 hours. This sample had a BET surface area of 418 m²/g.

TABLE 5

| 2Θ | d(Å) | I/I₀% |
|---|---|---|
| 6.92 | 12.76 | m |
| 11.70 | 7.56 | m |
| 19.60 | 4.53 | m |
| 23.50 | 3.78 | vs |
| 28.30 | 3.15 | m |
| 31.20 | 2.86 | vs |
| 35.83 | 2.5 | m |

Example 15

Choline aluminosilicate solution, 150 g, was placed in a beaker under a high speed stirrer. A solution was prepared by dissolving 1.29 g NaCl and 3.38 g Ba(OAc)₂ together in 20.01 g de-ionized water. This solution was added dropwise with vigorous stirring to the aluminosilicate solution. The solution eventually became cloudy and a suspension was formed by the end of the addition. After stirring further for 2 hours, the reaction mixture was distributed among nine Teflon-lined autoclaves and digested quiescently at 95, 125, and 150° C. for various times. All of the 95 and 125° C. products were UZM-7 by x-ray diffraction. The 150° C. samples were also UZM-7, but contained some SOD impurity. The diffraction lines for the UZM-7 formed at 95° C. and a digestion time of 10 days are given in Table 6 below. Elemental analysis on this sample yielded the compositional ratios Si/Al=1.91, Ba/Al=0.15, Na/Al=0.24, and N/Al=0.50. A sample digested at 95° C. for 17 days was calcined at 525° C. in air for 5 hours. This sample had a BET surface area of 388 m²/g.

TABLE 6

| 2Θ | d(Å) | I/I₀% |
|---|---|---|
| 7.06 | 12.51 | vs |
| 11.72 | 7.55 | m |
| 19.46 | 4.56 | m |
| 23.28 | 3.82 | vs |
| 28.16 | 3.17 | m |
| 30.84 | 2.90 | vs |
| 35.40 | 2.53 | m |

The invention claimed is:

1. A microporous crystalline zeolite having a three-dimensional framework of at least AlO₂ and SiO₂ tetrahedral units and an empirical composition in the as synthesized and anhydrous basis expressed by an empirical formula of:

$$M_m^{n+}R_r^{p+}Al_{1-x}E_xSi_yO_z$$

where M is at least one exchangeable cation selected from the group consisting of alkali, alkaline earth, and rare earth metals, "m" is the mole ratio of M to (Al+E) and varies from 0 to about 2.0, R is an organoammonium cation selected from the group consisting of choline, ethyltrimethylammonium (ETMA), diethyldimethylammonium (DEDMA), tetraethyl ammonium (TEA), tetrapropylammonium (TPA), trimethylpropylammonium, trimethylbutylammonium, dimethyldiethanolammonium, hexamethonium, and mixtures thereof, "r" is the mole ratio of R to (Al+E) and has a value of about 0.25 to about 4.0, "n" is the weighted average valence of M and has a value of about 1 to about 3, "p" is the weighted average valence of R and varies from 1 to about 2, E is an element selected from the group consisting of gallium, iron, boron and mixtures thereof, "x" is the mole fraction of E and has a value from 0 to about 1.0, "y" is the mole ratio of Si to (Al+E) and varies from greater than 1 to about 10 and "z" is the mole ratio of O to (Al+E) and has a value determined by the equation:

$$z=(m·n+r·p+3+4·y)/2$$

and is characterized in that it has the x-ray diffraction pattern having at least the d-spacings and intensities set forth in Table A:

TABLE A

| 2Θ | d(Å) | I/I0% |
|---|---|---|
| 6.79-8.03 | 13.00-11.00 | m-vs |
| 11.56-12.11 | 7.65-7.30 | w-s |
| 19.07-20.4 | 4.65-4.35 | m-s |
| 23.02-24.23 | 3.86-3.67 | m-vs |
| 26.43-28.13 | 3.37-3.17 | w-m |
| 30.48-31.94 | 2.93-2.80 | m-vs | and is thermally stable up to a temperature of at least 500° C.

2. The zeolite of claim 1 where M is selected from the group consisting of lithium, sodium, potassium, rubidium, cesium, calcium, strontium, barium and mixtures thereof.

3. The zeolite of claim 1 where "x" is zero.

4. The zeolite of claim 1 where the zeolite is thermally stable up to a temperature of at least 600° C.

5. The zeolite of claim 1 where R is choline.

6. The zeolite of claim 1 where R is choline and M is selected from the group consisting of Ba, Li, Na and mixtures thereof.

7. The zeolite of claim 1 where R is DEDMA.

8. The zeolite of claim 1 where R is DEDMA and M is selected from the group consisting of K, Li and mixtures thereof.

9. A process for preparing a microporous crystalline zeolite having a three-dimensional framework of at least AlO₂ and SiO₂ tetrahedral units and an empirical composition in the as synthesized and anhydrous basis expressed by an empirical formula of:

$$M_m^{n+}R_r^{p+}Al_{1-x}E_xSi_yO_z$$

where M is at least one exchangeable cation selected from the group consisting of alkali, alkaline earth, and rare earth metals, "m" is the mole ratio of M to (Al+E) and varies from 0 to about 2.0, R is an organoammonium cation selected from the group choline, ethyltrimethylammonium (ETMA), diethyldimethyl ammonium (DEDMA), tetraethyl ammonium (TEA), tetrapropylammonium (TPA), trimethylpropylammonium, trimethylbutylammonium, dimethyldiethanolammonium, hexamethonium cations and mixtures thereof, "r" is the mole ratio of R to (Al+E) and has a value of about 0.25 to about 4.0, "n" is the weighted average valence of M and has a value of about 1 to about 3, "p" is the weighted average valence of R, E is an element selected from the group consisting of gallium, iron, boron and mixtures thereof, "x" is the mole fraction of E and has a value from 0 to about 1.0, "y" is the mole ratio of Si to (Al+E) and varies from greater than 1 to about 10 and "z" is the mole ratio of O to (Al+E) and has a value determined by the equation:

$$z=(m·n+r·p+3+4·y)/2$$

and is characterized in that it has the x-ray diffraction pattern having at least the d-spacings and intensities set forth in Table A:

TABLE A

| 2Θ | d(Å) | I/I0% |
|---|---|---|
| 6.79-8.03 | 13.00-11.00 | m-vs |
| 11.56-12.11 | 7.65-7.30 | w-s |
| 19.07-20.4 | 4.65-4.35 | m-s |
| 23.02-24.23 | 3.86-3.67 | m-vs |
| 26.43-28.13 | 3.37-3.17 | w-m |
| 30.48-31.94 | 2.93-2.80 | m-vs | and is thermally stable up to a temperature of at least 500° C.; the process comprising forming a reaction mixture containing reactive sources of M, R, Al, Si and optionally E and heating the reaction mixture at a temperature of about 60° C. to about 175° C., for a time sufficient to form the zeolite, the reaction mixture having a composition expressed in terms of mole ratios of the oxides of:

$$aM_{2/n}O:bR_{2/p}O:1-cAl_2O_3:cE_2O_3:dSiO_2:eH_2O$$

where "a" has a value of about 0.0 to about 4.0, "b" has a value of about 1.0 to about 30, "c" has a value of 0 to about 1.0, "d" has a value of about 2 to about 30, "e" has a value of about 20 to about 2000.

10. The process of claim 9 where M is selected from the group consisting of lithium, cesium, sodium, potassium, rubidium, strontium, barium and mixtures thereof.

11. The process of claim 9 where the source of M is selected from the group consisting of halide salts, nitrate salts, acetate salts, hydroxides, sulfate salts and mixtures thereof.

12. The process of claim 9 where the source of E is selected from the group consisting of alkali borates, boric acid, precipitated gallium oxyhydroxide, gallium sulfate, ferric sulfate, ferric chloride and mixtures thereof.

13. The process of claim 9 where the aluminum source is selected from the group consisting of aluminum isopropoxide, aluminum sec-butoxide, precipitated alumina, $Al(OH)_3$, aluminum metal and aluminum salts.

14. The process of claim 9 where the silicon source is selected from the group consisting of tetraethyorthosilicate, fumed silica, colloidal silica and precipitated silica.

15. The process of claim 9 where the reaction mixture is reacted at a temperature of about 90° C. to about 150° C. for a time of about 1 day to about 3 weeks.

16. The process of claim 9 where R is choline.

17. The process of claim 9 where R is diethyldimethylammonium.

18. The process of claim 9 where R is choline and M is selected from the group consisting of Ba, Li, Na and mixtures thereof.

19. The process of claim 9 where R is diethyldimethylammonium and M is selected from the group consisting of K, Li, and mixtures thereof.

20. The process of claim 9 where R is a combination of choline and at least one organoammonium cation selected from the group consisting of TEA, TPA, ETMA, DEDMA, trimethylpropylammonium, trimethylbutylammonium, hexamethonium or dimethyldiethanolammonium.

21. The process of claim 9 further comprising adding UZM-7 seeds to the reaction mixture.

* * * * *